United States Patent [19]

Lancaster

[11] 4,215,458

[45] Aug. 5, 1980

[54] EXTRACTOR TOOL

[76] Inventor: Robert D. Lancaster, 4902 Mayfair, Bellaire, Tex. 77401

[21] Appl. No.: 10,635

[22] Filed: Feb. 9, 1979

[51] Int. Cl.² ............................................. B23P 19/04
[52] U.S. Cl. ................................................. 29/213 R
[58] Field of Search ........................... 29/213; 137/318

[56] References Cited

U.S. PATENT DOCUMENTS

| 2,647,419 | 8/1953 | Dickason | 29/213 |
| 2,770,532 | 11/1956 | Mason | 29/213 |
| 2,870,629 | 1/1959 | Willis | 29/213 |
| 3,031,742 | 5/1962 | Auer | 29/213 |
| 3,995,655 | 12/1976 | Sands | 137/318 |

*Primary Examiner*—James L. Jones, Jr.

*Attorney, Agent, or Firm*—Bill B. Berryhill

[57] ABSTRACT

A tool for handling elements to be installed in or removed from a pressurized vessel may comprise: a housing adapted for connection and fluid communication with the pressurized vessel; a carrier assembly disposed in the housing for reciprocation therein to which elements may be attached for installation in or removal from the pressurized vessel; and first and second operator assemblies carried by the housing. The first operator assembly is engageable with the carrier assembly for reciprocation thereof between first and second terminal positions. A second operator assembly is engageable with the carrier assembly for selective rotation of the elements attached thereto.

15 Claims, 5 Drawing Figures

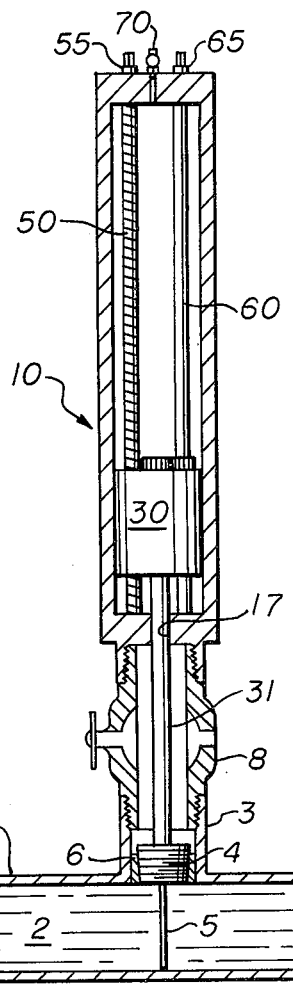
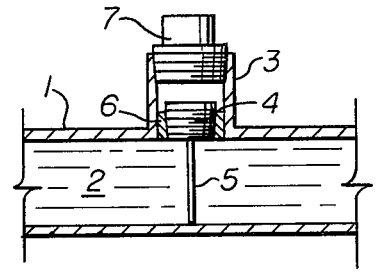
fig.1
fig.2
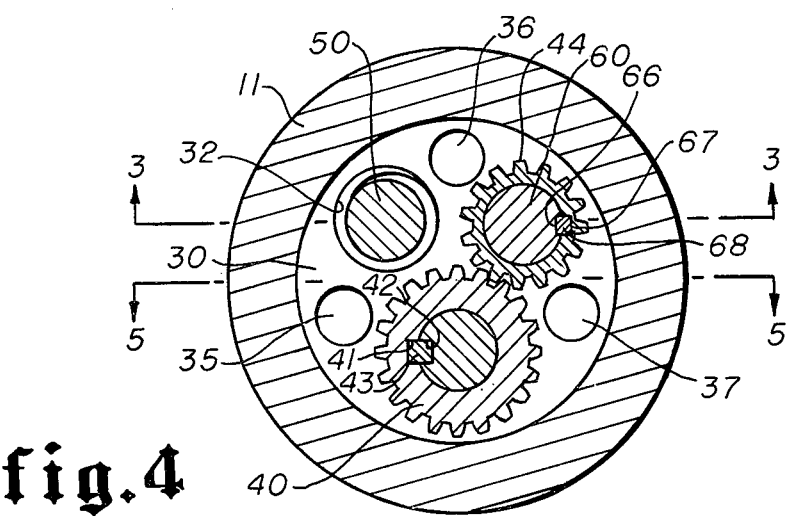
fig.4

EXTRACTOR TOOL

BACKGROUND OF THE INVENTION

1. Field of the Invention

The present invention pertains to tools for handling elements to be installed in or removed from pressurized vessels. Specifically, it pertains to a tool for installing or removing coupons, anodes and like elements in a pressurized vessel, pipeline or the like.

2. Brief Description of the Prior Art

Frequently it is desirable to insert into a pipeline, or other pressurized vessel, a coupon from which can be measured the rate of corrosion due to the fluids being transported through the pipeline or vessel. It may also be desirable to insert an anode into the pipeline or vessel for retarding corrosion of the vessel material. In addition, other elements such as temperature probes, transducers, etc. are from time to time inserted into such pressurized environments. If the pipeline or other vessel is empty, installation of such coupons, anodes, probes, etc. is a relatively easy task. However, if the pipeline or other vessel is in operation, the pressure therein increases the difficulty and hazard of such a task.

Since it is expensive to arrest the flow in and evacuate fluids from an operating pipeline or vessel, it is desirable that methods and apparatus be provided which will allow installation or removal of elements from the pipeline or vessel while it continues to operate. Accordingly, various extractor tools have been developed in recent years to accomplish such a task. One such tool is shown in U.S. Pat. No. 2,770,532. With this extractor tool, the element is inserted or removed by a rack and pinion arrangement. The tool is designed to be left in place at all times and to retrieve the coupon, anode or other elements, it is necessary to rotate a disc on which the housing is disposed. The length of such a tool is unduly long. Furthermore, if a number of elements are required, the cost of supplying a tool for each element may become prohibitive.

In U.S. Pat. No. 2,870,629, an extractor tool is disclosed which is designed for removal and use at a number of locations. This is made possible through the use of a check valve arrangement. Reciprocation of the mechanism for inserting or removing the coupon is accomplished by applying pressure to a piston like carrier. The operation of such a tool requires a source of fluid pressure and the design is relatively expensive to manufacture and maintain.

Another pressure-operated extractor tool is shown in U.S. Pat. No. 3,031,742. This tool is actuated by pressure directly from the pipeline or vessel in which the element is installed. Thus, it is not necessary to have an independent source of pressure. This tool is also relatively complex to manufacture and maintain. Furthermore, to engage a coupon or other element with a receiving fitting in the vessel or to remove one therefrom, it is necessary to rotate the entire tool.

Very recently, another extractor tool has been developed by Brown Oil Tools, Inc., which is removable and manually operable, eliminating some of the disadvantages of prior extractor tools. Such a tool is equipped with two mechanisms, one for providing a relatively large amount of reciprocal movement for inserting and removing the coupon or other element and the second for providing rotational movement of the coupon or other element upon engagement with a fitting by which said element is held in the pipeline or vessel. The first mechanism involves a rack and pinion having a crank, rotation of which causes the rack to move in and out for installing and removing the element. When the element is extended into the pipeline or vessel by a sufficient amount, the second mechanism, a worm and worm wheel arrangement, is engaged and operated. Rotation of the worm which engages a worm wheel attached to the element holder causes the holder to rotate for threadedly engaging a fitting to hold the element in place.

While the aforementioned tool is better in some respects to the prior art, it has certain inherent problems. At least two of these problems are due to the rack and pinion mechanism. Such a mechanism causes the tool to be unduly long. This is particularly a problem when the coupon or other element to be installed is to be installed in a fitting beneath a pipeline, requiring extensive soil removal, or where there are limited clearances between the pipeline and adjacent equipment. Another problem is the danger when pressure in the tool is not equalized with the pipeline upon removal of the element. In such a case, pipeline pressure may cause the rack to be quickly forced to an extended position, rapidly rotating the crank with potential danger to the operator and damage to the tool. Another disadavantage is the fact that the crank for operation of the reciprocating mechanism and wheel for operation of the rotating mechanism may be separated by several feet in large models, requiring two operators.

The fact that extractor tools for handling coupons, anodes, and the like during installation in and removal from pressurized pipeline or vessels continues to be developed, is an indication of a need for better tools. While prior art tools have evolved for the better, they still have characteristics which are not totally acceptable.

SUMMARY OF THE INVENTION

In the present invention, an extractor tool is disclosed which is provided with two mechanisms, one for imparting reciprocal movement and the other for imparting rotational movement. Reciprocal movement is for moving the coupon, anode or other element into or out of the opening of a pressurized pipeline or vessel. The rotating mechanism is for rotating the coupon or anode holders or other elements for threaded and sealing engagement with a fitting provided in the pipeline or vessel. The rotating mechanism can also be used for turning a drill or the like in hot tapping procedures.

The tool includes a housing adapted for connection with a valve or other fitting so as to be in fluid communication with the pipeline or vessel in which the coupon is to be inserted. It also includes a carrier assembly disposed in the housing for reciprocation therein, having means for engaging the coupon, anode, or other element, and first and second operator assemblies carried by the housing. The first operator assembly is engageable with the carrier assembly for reciprocation thereof between first and second terminal positions. The second operator assembly is engageable with a carrier assembly for rotation of a portion thereof so as to impart rotation to the coupon, anode or other element for engaging or disengaging the fitting by which it is held in the pipeline or other vessel.

The arrangement of the components of the present invention results in a tool length substantially shorter than the rack and pinion tools of the prior art. In addition, the wheels or levers for activating the first and second operator assemblies may be close together so that a single operator can manipulate the tool. In addition, the reciprocating mechanism includes a self-locking threaded member which prevents reciprocation of the mechanism in cases where the vessel pressure may be communicated to the tool. Many other objects and advantages of the invention will be apparent from reading the description which follows in conjunction with the accompanying drawings.

BRIEF DESCRIPTION OF THE DRAWINGS

FIG. 1 is a sectional view of a pipeline having a fitting in which is installed a coupon for determining the corrosion rate of materials in the pipeline;

FIG. 2 is a sectional view of the pipeline shown in FIG. 1 showing an extractor tool, according to a preferred embodiment of the invention, attached to the pipeline fitting with a valve therebetween;

FIG. 4 is a cross-sectional view, taken along line 4—4 of FIG. 3, of the extractor tool according to a preferred embodiment of the invention.

DESCRIPTION OF A PREFERRED EMBODIMENT

Figure 3:
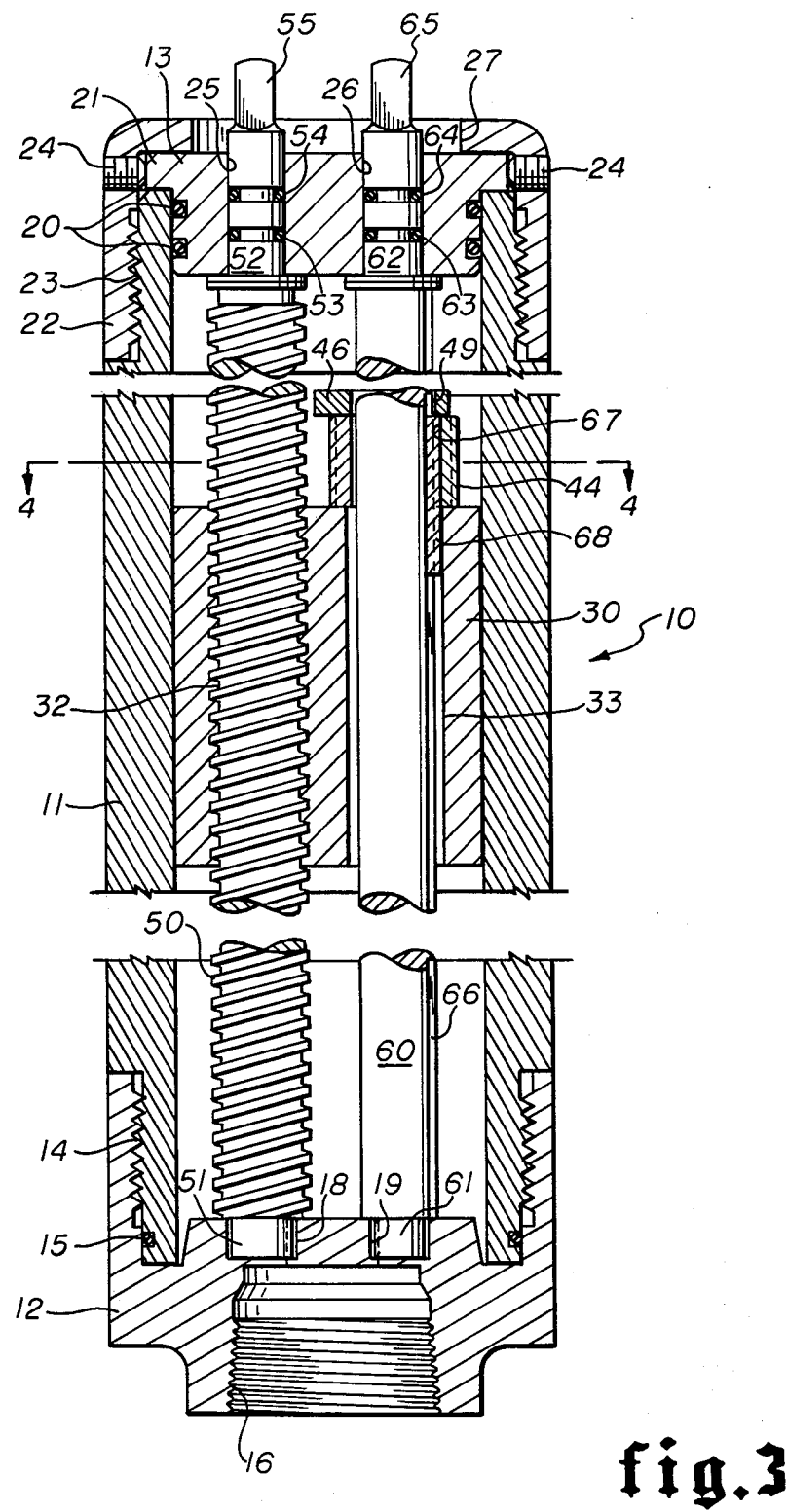
FIG. 3 is an elevation view of the extractor tool of the present invention taken along line 3—3 of FIG. 4, partially in section and certain components of which are broken away for a more complete understanding thereof.

Referring first to FIG. 1, there is shown a pipeline 1 represented as being under pressure with a fluid 2 passing therethrough. The pipeline 1 is provided with a perpendicular fitting 3 in the opening of which is installed a coupon holder 4 having attached thereto a coupon 5. The coupon may be for the purpose of determining the rate of corrosion due to the fluids 2 in the pipeline. Instead of the coupon 5, the holder 4 could support a corrosion protection anode, a temperature probe or any other element conventionally placed in pipelines or pressurized vessels. As shown, the coupon holder 4 is held in place by engagement with a threaded bushing 6 provided in the fitting 3. This connection is usually provided with some sort of seal so that when the holder 4 is properly installed, fluids are prevented from escaping from the pipeline 1. As shown in FIG. 1, a protective plug 7 may be placed in the end of the fitting 3.

It is frequently necessary to remove, replace or install coupons 5 or other elements in the pipeline 1 while it remains in service. The extractor tool of the present invention is designed for this purpose. While the extractor tool of the present invention will be described herein for handling the coupon 5 in pipeline 1 it is to be understood that it may be used for handling other elements of any type for use in a pressurized vessel or container.

It may be used with reaming or cleaning elements. It may also be used to manipulate drills in hot tapping of pressurized vessels or containers. The term "element" as used herein is intended to cover all of these items.

Referring now to FIG. 2, there is shown an extractor tool 10, according to a preferred embodiment of the invention, which has been attached to the pipeline 1 for removal of coupon holder 4 and coupon 5 therefrom. As shown, the plug 7 has been removed and a valve 8 attached to the fitting 3. The valve may be of any suitable type, the one illustrated being of the ball type. The extractor tool 10 of the present invention may then be attached to the ball valve 8 so as to provide communication, as will be more fully understood hereafter, between the extractor tool 10 and the opening through fitting 3 into the pipeline 1.

Figure 5:
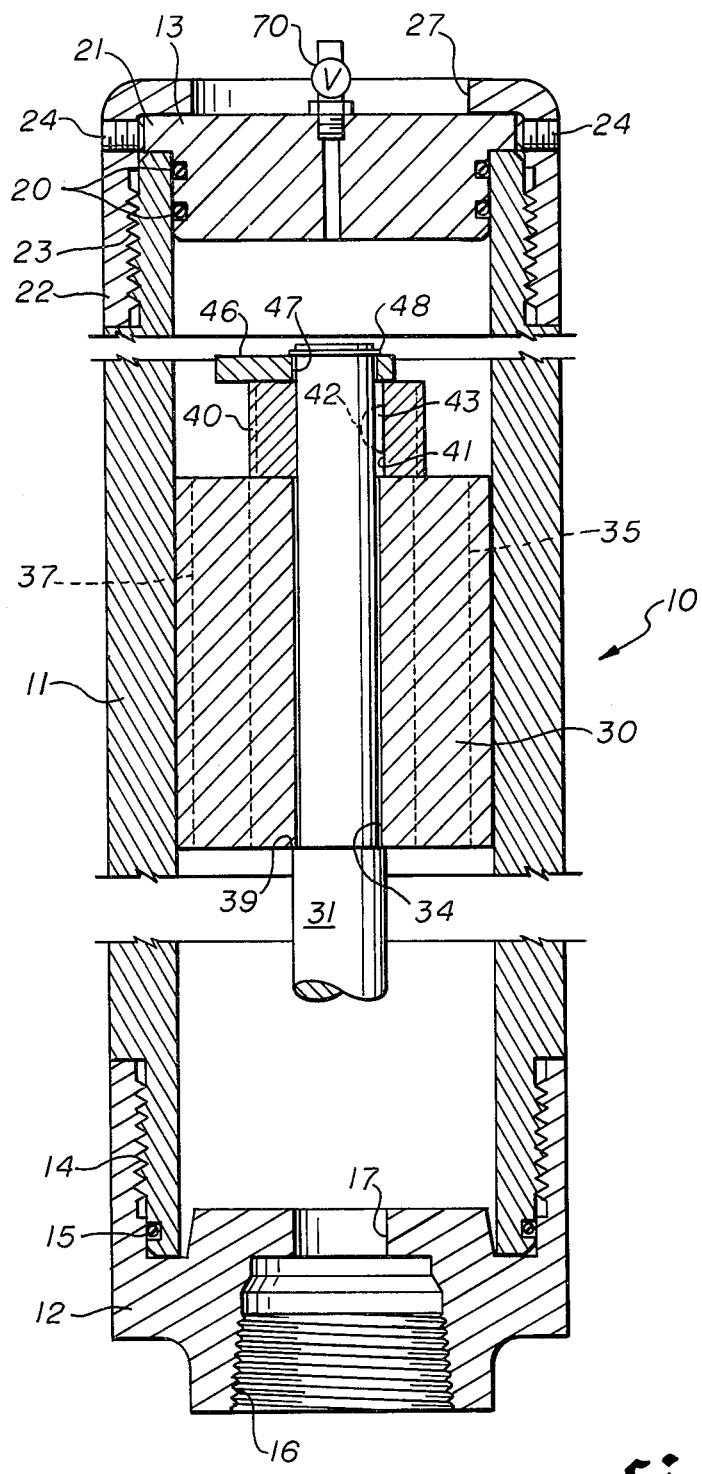
FIG. 5 is an elevation view similar to FIG. 3 but taken along line 5—5 of FIG. 4.

Referring also now to FIGS. 3, 4 and 5, the extractor tool 10 of the present invention includes a housing assembly made up of tubular body 11 having a fitting adaptor 12 at one end and closed at the other end by an end plate 13. The adaptor 12 may be connected to the body 11 by a threaded connection 14 and provided with an annular seal 15. The adaptor 12 is also provided with internal threads 16 by which it may be attached to the valve 8, as in FIG. 2, or any other manner for connection with the fitting 3. The adaptor 12 is also provided with an opening 17 (see FIG. 5) through which communication may be established between the extractor tool 10 and the opening of fitting 3. The opening 17 may be offset from the central axis of the extractor tool 10 to correspond with other components of the tool as will be more fully understood hereafter. Also provided in the adaptor 12 are closed end holes 18 and 19 which may serve as journal boxes for a pair of shafts longitudinally disposed in the tool.

The end plate 13 can be attached to the body 11 in any suitable manner. In the exemplary embodiment, the end plate is a cylindrical member whose outside diameter is slightly less than the inside diameter of body 11, which when provided with seals 20 result in a pressure sealing fit. The end plate 13 may also be provided with an annular flange 21 by which the plate may rest against the upper end of tubular body 11. The plate 13 may be held in this position by a retaining cap 22 threadedly connected at 23 to the body 11. The retaining cap 22 may be provided with set screws 24 around its periphery for engagement with the flange portion 21 of the end plate for holding the end plate in a particular orientation. Extending through the end plate 13 is a pair of holes 25 and 26 for receiving the ends of a pair of shafts as will be more fully described hereafter. It will be noted that the end cap 22 has a central opening 27 through which the shafts may project.

Longitudinally disposed within the extractor tool housing 11 is a carrier assembly which includes a cylindrical head member 30 and a rod member 31 (see FIG. 5). The outside diameter of the head member 30 is slightly less than the inside diameter of the housing body 11 permitting the head member 30 to freely slide or reciprocate within the housing. The length of the head member 30 should be great enough to prevent cocking of the carrier assembly, especially the rod member 31. The head member 30 is provided with several longitudinal holes. One of them 32 is internally threaded for engagement with a threaded shaft 50 to be more fully described hereafter. Another one 33 is a smooth borehole to slidingly receive a smooth shaft 60 which will be more fully described hereafter. A third hole 34 (see FIG. 5) also has a smooth bore for receiving the upper end of rod member 31. The carrier head 30 may also be provided with other holes 35, 36 and 37 (see FIG. 4) the purpose of which is simply to equalize pressure in all parts of the housing.

The lower end of the rod member 31 (not shown in FIGS. 3 and 5 but depicted in FIG. 2) is provided with any suitable means of connection for connecting the rod member to the coupon holder 4 or any other type of element to be installed in or removed from a pressurized vessel. There are several types of connections available in the prior art which are suitable for this use. Therefore, no specific type will be described herein. The diameter of the upper end of rod 31 is slightly less than the portion below head member 30 creating an annular shoulder 39 (see FIG. 5) which aids in holding the rod 31 in a fixed longitudinal position, relative to the head member 30, when assembled. The diameter of the rod member 31 above shoulder 39 is slightly less than the internal diameter of the hole 34 which it engages, allowing rotation of the rod member 31 relative to head member 30. The upper end of rod member 31 projects through head member for engagement with a spur gear 40 which forms part of an operator assembly which will be more fully described hereafter. The spur gear 40 and the upper end of rod member 31 are provided with slots 41 and 42 which in cooperation with a Woodruff key 43 prevents relative rotation between the spur gear 40 and rod member 31. Engaging spur gear 40 is another spur gear 44 (see FIGS. 3 and 4), which also forms a part of an operator assembly to be more fully described hereafter. Both gears 40 and 44 and the rod member 31 are held in place at the upper end of head member 30 by an elongated combination washer and cap member 46. This member is provided with a borehole 47 through which the upper end of rod member 31 projects for engagement of an annular slot therein by a snap ring 48. Offset from the through bore 47 is a counterbored hole 49 for receiving the hub of gear member 44 and through which extends smooth shaft 60. Thus, the combination washer and cap member 46 holds the gears 40 and 44 and the rod member 31 in a fixed longitudinal relationship.

There are two operator assemblies in the extractor tool 10. The first includes the threaded shaft 50 which threadedly engages the threaded hole 32 through carrier head member 30 having a lower journal 51 received by the journal box 18 in adaptor 12 (see FIG. 3). The upper end of the shaft 50 is provided with a journal 52 which is received in the hole 25 through end plate 13. The journals 51 and 52 are of diameters slightly less than the holes in which they are received so as to allow rotation relative to adaptor 12 and end plate 13. Annular seal members 53 and 54 may be provided between the upper journal and hole 25 to seal the interior of the tool from the surrounding atmosphere. The upper end of the threaded shaft 50 is machined, as shown at 55, to receive an operating wheel, lever, power wrench or the like (not shown) for rotating threaded shaft 50. It will, of course, be understood that due to the threaded engagement between shaft 50 and head member hole 32, rotation of the shaft 50 will cause the carrier assembly, including carrier head 30 and rod member 31 to reciprocate between a first terminal position, as illustrated in FIGS. 3 and 5, and a second terminal position as illustrated in FIG. 2.

The second operator assembly includes the smooth shaft 60 having a lower journal 61 received in the journal box 19 provided in adaptor 12 (see FIG. 3). The shaft member 60 is also provided with an upper journal 62 received in the hole 26 which extends through the end plate 13. The diameter of journals 61 and 62 are slightly less than the holes in which they are received allowing rotation of shaft 60 relative to adaptor 12 and end plate 13. Like with the threaded shaft 50 of the first operator assembly, annular seals 63 and 64 are provided between journals 62 and hole 26 to seal the interior of the extractor tool 10 from the surrounding atmosphere.

Also like with the threaded shaft 50, shaft 60 is provided with a machined end 65 to receive an operating member by which the shaft 60 may be rotated.

The second operator assembly also includes a rotating mechanism, including spur gears 40 and 44. The attachment of the spur gear 40 and the mounting of both of the spur gears has already been described. The spur gear 44 surrounds the shaft 60 in a sliding fit. However, the shaft 60 and spur gear 44 are provided with mutually aligned keyways 66 and 67, respectively, for receiving a key 68 (affixed to spur gear 44) which prevents rotation of the spur gear 44 relative to the shaft 60. Thus, spur gear 44 and key 68 can reciprocate along rod 60 but cannot rotate unless the rod 60 also rotates.

It will thus be understood that regardless of the position of the carrier assembly and the spur gear 44 which moves longitudinally therewith, spur gear 44 is always in position to be rotated upon rotation of shaft 60. It will also be understood that rotation of rod 60 by engagement of the machined operating end 65 will cause rotation of spur gear 44 which will in turn rotate spur gear 40. Rotation of spur gear 40 will cause rotation of rod member 31 with respect to the head member 30.

If it is necessary to disassemble the extractor 10 it can be done very easily by first disengaging set screws 24, removing retainer cap 22 and the end plate 13. Then the carrier assembly and both operating assemblies, including shafts 50 and 60 can be simply lifted out of the housing through the open upper end thereof. Assembly would be just the reverse.

To remove an element installed in a pressurized vessel such as the coupon 5 and coupon holder 4 shown in FIG. 2, the extractor tool 10 would be attached to the pipeline 1 such as is shown in FIG. 2 with an intervening valve 8 between the fitting 3 and the extractor tool 10. However, the carrier assembly, including the head 30 and rod member 31 would be in the first terminal position illustrated in FIG. 3. Then an operating wheel or lever would be engaged with the operating end 55 of the threaded shaft 50 of the first operating assembly. Rotation of the shaft 50 would cause the head member 30 to move downwardly toward the second terminal position illustrated in FIG. 2. As this occurs, the lower end of rod member 31 would proceed through the opening 17 through valve 8 into the fitting 3 where it would finally contact the coupon holder 4. At this point a lever or other operating member would be placed on the operating end 65 of the second operator assembly shaft 60 and the shaft 60 rotated in the desired direction. As previously described, rotation of the shaft 60 will cause rotation of rod member 31 so that the engagement means on the lower end thereof would properly engage the coupon holder 4. Upon proper engagement, the shaft member 60 would be rotated in whatever direction is necessary to disengage the coupon holder 4 from the bushing 6 within fitting 3. During the manipulation of rod 31 with coupon holder 4, it might be necessary to adjust the longitudinal position of the carrier assembly within the tool by slight movement of threaded shaft 50.

Once the coupon holder 4 is properly engaged by rod member 31 and disengaged from the bushing 6, the first operator assembly shaft 50 is rotated in the opposite direction, causing the carrier assembly to move from the second terminal position, shown in FIG. 2, back toward the first terminal position illustrated in FIG. 3. As this occurs, the coupon holder 4 and coupon 5 move upwardly through the valve 8 until it is possible to close the valve. After the valve 8 is closed and the tool is bled through vent valve 70 (see FIGS. 2 and 5), the extractor tool 10 can be removed for access to the coupon holder 4 and coupon 5. If the coupon and coupon holder need to be replaced with others or other types of elements, the installation procedure would simply be the reverse of the removal.

An interesting feature of the tool is the ability to displace pipeline fluids from the tool back into the pipeline without disturbing the longitudinal position of the carrier assembly. Upon connecting a source of nitrogen or some other inert fluid to the vent valve 70, the valve 70 can be opened allowing the nitrogen to enter the tool forcing fluids therein back into the pipeline. This can be done upon installation of a coupon just prior to engagement of the coupon with the pipeline fitting, or upon the carrier assembly reaching the first terminal position, prior to closing the valve and removing the tool from the valve.

As can be seen from the foregoing description of a preferred embodiment, the present invention offers an extractor tool which is unique in several respects. For one, it is considerably shorter than extractor tools of the prior art, particularly those with rack and pinion mechanisms. In fact, it is almost half as long as some of the rack and pinion extractor tools of the prior art. In addition, the first and second operator assemblies are located so that they may be operated simultaneously by one man. Furthermore, due to the self-locking feature of the threaded engagement between the first operating assembly shaft and threaded hole in the carrier assembly, the danger of an operating wheel or lever injuring the operator of the carrier assembly damaging the tool is eliminated. The arrangements of the components of the tool and the pressure-balanced construction of the carrier assembly makes the tool easy to operate. Not only is it easy to operate, it is relatively simple to maufacture, install and repair. Its assembly and disassembly are relatively simple. Furthermore, it is easily adapted for use with different size pipelines, vessels and elements. By simply changing out the tubular body 11, threaded shaft 50 and smooth shaft 60 the length of the tool can be changed to accommodate the vessel or element with which it is to be used. If desired, the tool can be adapted for operation at the end opposite the one described by providing a right angle drive near the fitting adaptor 12.

A preferred embodiment of the extractor tool of the present invention has been described herein for use in handling a coupon and coupon holder being installed in or removed from a pressurized pipeline. Of course, other elements for use in pressurized vessels, such as anodes, temperature probes, etc. can be handled with the same extractor tool. Furthermore, the extractor tool can be used as a hot tapping tool by attaching a drill to the rod member 31. Since the second or rotating operator assembly is independent of the first reciprocating operator assembly, rotation of the drill may be accomplished at any point between the terminal positions of the tool. The self-locking characteristic of the reciprocating operator assembly prevents harm to the operator or tool during this operation. In addition, there are many other variations of the extractor tool which can be made without departing from the spirit of the invention. Accordingly, it is intended that the scope of the invention be limited only by the claims which follow.

I claim:

1. A tool for handling elements to be used with a pressurized vessel comprising:

housing means having connection means on one end thereof for connecting said housing in fluid communication with an opening in said vessel;

carrier means disposed in said housing means for reciprocation therein having engagement means at one end thereof for engagement with said elements;

first operator means carried by said housing and engageable with said carrier means for reciprocation of said carrier means between a first terminal position in which said elements, if engaged by said engagement means, are removed from said vessel and a second position in which said elements, if engaged by said engagement means, are inserted within said vessel through said opening thereinto; and second operator means carried by said housing and engageable with said carrier means for rotation of said elements.

2. A tool as set forth in claim 1 in which said first operator means includes a threaded rotatable first shaft longitudinally disposed in said housing means threadedly engaging a threaded hole provided in said carrier means, one end of said first shaft being engageable externally of said housing means for translating rotation of said first shaft to said reciprocation of said carrier means.

3. A tool as set forth in claim 2 in which said second operator means includes a rotating mechanism, a portion of which is carried by said carrier means within said housing means, and a rotatable second shaft engaging said rotating mechanism, one end of said second shaft being engageable externally of said housing means and rotation of which results in activation of said rotating mechanism for rotation of said elements when engaged by said engagement means.

4. A tool as set forth in claim 3 in which said first and second shafts are independently rotatable so that upon said reciprocation of said carrier means by rotation of said first shaft, said elements may be selectively rotated by said second shaft.

5. A tool as set forth in claim 3 in which said carrier means comprises a rod portion and an enlarged head portion, said threaded hole being provided in said head portion, said engagement means being provided on one end of said rod portion, said rod portion being attached to said head portion for reciprocation therewith and for rotation relative thereto in response to said rotation of said second shaft.

6. A tool for handling elements to be used with a pressurized vessel comprising:

a tubular housing, one end of which is provided with means for connecting said housing in fluid communication with an opening in said vessel, the opposite end of which is closed;

a carrier assembly disposed for reciprocation within said housing including a rod member and an enlarged head member, one end of said rod member being provided with means for releasably holding said elements to be installed or removed, the opposite end of said rod member being attached to said head member so as to permit rotation of said rod member relative to said head member;

first operator means carried by said housing engageable with said carrier head member and actuatable externally of said housing for reciprocal movement of said carrier assembly between a first terminal position in which said one end of said rod member is within said housing and a second terminal position in which said one end of said rod member extends through said pressure vessel opening; and second operator means carried by said housing engageable with said opposite end of said rod member and actuatable externally of said housing for rotating said rod member relative to said head member.

7. A tool as set forth in claim 6 in which said first operator means comprises a threaded shaft longitudinally disposed in said housing and engaging a corresponding threaded hole provided in said carrier head member, rotation of said threaded shaft effecting said reciprocation of said carrier assembly.

8. A tool as set forth in claim 7 in which said second operator means comprises a second shaft parallel to said threaded shaft and slidingly engaging a corresponding hole provided in said carrier head member, rotation of said second shaft effecting said rotation of said carrier rod member.

9. A tool as set forth in claim 8 in which said opposite end of said housing is sealingly closed by an end plate through which one end of said threaded and second shafts extend for actuation of said first and second operator means.

10. A tool as set forth in claim 9 in which said end plate is removably attached to said housing, removal of said plate permitting removal of said carrier assembly and said first and second operator means.

11. A tool as set forth in claim 8 in which said second operator means comprises a first gear member attached to said opposite end of said carrier rod member, a second gear member engaging said first gear member and mounted on said second shaft.

12. A tool as set forth in claim 11 in which said second gear member is mounted on said second shaft by key and keyway means, permitting axial movement of said second shaft relative to said second gear member but preventing relative rotation therebetween.

13. A tool as set forth in claim 6 in which said second operator means comprises a first member engaging said carrier rod member and a second member engaging said first member and mounted on a shaft rotation of which effects said rotation of said carrier rod member.

14. A tool as set forth in claim 13 in which said second member is mounted on said shaft for relative axial movement thereon but non-rotatable relative thereto.

15. A tool as set forth in claim 14 in which said shaft is longitudinally disposed within said housing and projecting through a hole in said carrier head member permitting relative sliding longitudinal movement therebetween.

* * * * *